US009705989B2

(12) United States Patent
Sipola et al.

(10) Patent No.: US 9,705,989 B2
(45) Date of Patent: Jul. 11, 2017

(54) PAIRING OF DEVICES

(71) Applicant: Polar Electro Oy, Kempele (FI)

(72) Inventors: Matti Sipola, Oulu (FI); Erkki Silvola, Oulunsalo (FI); Juha Onkila, Oulu (FI); Petteri Siekkinen, Kempele (FI)

(73) Assignee: POLAR ELECTRO OY, Kempele (FI)

( * ) Notice: Subject to any disclaimer, the term of this patent is extended or adjusted under 35 U.S.C. 154(b) by 287 days.

(21) Appl. No.: 14/026,519

(22) Filed: Sep. 13, 2013

(65) Prior Publication Data

US 2015/0081763 A1 Mar. 19, 2015

(51) Int. Cl.
| | |
|---|---|
| G06F 15/173 | (2006.01) |
| H04L 29/08 | (2006.01) |
| A61B 5/00 | (2006.01) |
| H04W 12/08 | (2009.01) |
| G06Q 10/06 | (2012.01) |
| H04L 29/06 | (2006.01) |

(52) U.S. Cl.
CPC .............. *H04L 67/12* (2013.01); *A61B 5/00* (2013.01); *A61B 5/0002* (2013.01); *G06Q 10/0639* (2013.01); *H04W 12/08* (2013.01); *H04L 63/101* (2013.01)

(58) Field of Classification Search
CPC ........ H04L 67/42; H04L 67/12; H04L 63/101
USPC ........................................................ 709/203
See application file for complete search history.

(56) References Cited

U.S. PATENT DOCUMENTS

| 9,026,053 | B2* | 5/2015 | Molettiere | ............... H04B 7/26 455/41.2 |
|---|---|---|---|---|
| 2010/0199338 | A1* | 8/2010 | Craddock | ............... G06F 21/31 726/7 |
| 2012/0182939 | A1 | 7/2012 | Rajan et al. | |
| 2014/0375428 | A1* | 12/2014 | Park | ................... G06K 7/10237 340/10.1 |
| 2016/0037345 | A1* | 2/2016 | Margadoudakis | .. H04L 63/0853 455/411 |

FOREIGN PATENT DOCUMENTS

WO 2010077851 A2 7/2010

OTHER PUBLICATIONS

European Search Report, Application No. EP 14182134, 2 pages, Jan. 22, 2015.

* cited by examiner

*Primary Examiner* — Vivek Srivastava
*Assistant Examiner* — Karina J Garcia-Ching
(74) *Attorney, Agent, or Firm* — Hoffmann & Baron, LLP

(57) ABSTRACT

A server computer to provide a web service including exercise data user accounts, acquire and store a unique device identifier of at least one physiological sensor device, associate each of the acquired at least one device identifier with one of the exercise data user accounts, detect that an exercise application of a user terminal successfully accesses a specific exercise data user account, and provide the user terminal with the at least one device identifier which is associated with the specific exercise data user account. There is further provided a user terminal to successfully access the specific exercise data user account in the web service, acquire the at least one device identifier from the web service, and apply the acquired at least one device identifier in determining whether or not to allow the user terminal to wirelessly pair with a physiological sensor device.

23 Claims, 3 Drawing Sheets

PAIRING OF DEVICES

BACKGROUND

Field

The invention relates generally to pairing of devices. More particularly, the invention relates to pairing of an exercise device with a user terminal.

Description of the Related Art

Pairing of devices is often a cumbersome task as it may require user actions or proximity technologies, for example. The user actions decrease the user comfort, and proximity technologies tend to increase the complexity of the devices. Furthermore, in some cases, the user interface of at least one of the devices to be paired may be insufficient for pairing.

SUMMARY

According to an aspect of the invention, there is provided a system as specified in claim 1.

According to an aspect of the invention, there is provided an apparatus as specified in claim 17.

According to an aspect of the invention, there is provided a computer program product as specified in claim 23.

According to an aspect of the invention, there is provided a computer-readable distribution medium carrying the above-mentioned computer program product.

According to an aspect of the invention, there are provided a system and an apparatus comprising means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

It is common to wear a personal training computer (TC) during an exercise. The TC may be a wrist worn device, for example. The exerciser may monitor the performance data of the exerciser, such as heart activity data, from the TC during the exercise in real time. This may take place by the training computer receiving information from an exercise sensor, such as heart rate-related information from a heart rate monitor, location specific information from a foot pod or from a global positioning system (GPS) receiver, cadence data from a corresponding monitoring device, pace/speed related data from the GPS/foot pod, etc. The training computer may store the data as exercise data which the user (exerciser) may use in post-analysis of the performed exercise. Such post-analysis may be at some level processed in the TC directly, such as in the wrist computer. However, often the TC is found too small and to lack computational efficiency. Therefore, for a more accurate and in-depth analysis, the exercise data is typically transferred from the training computer and/or exercise sensor to a web-based service located in a server of a network.

Figure 1:
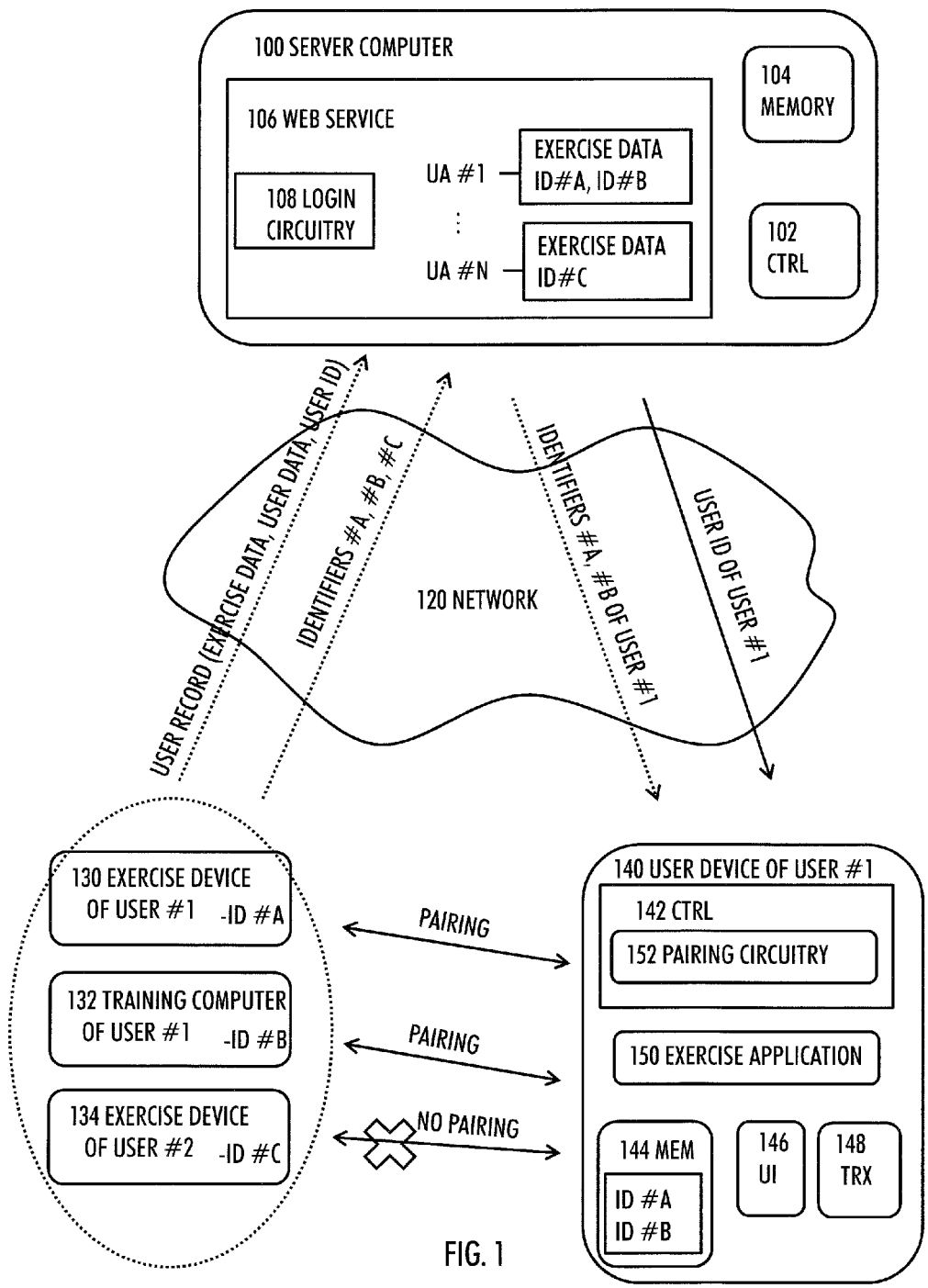
FIG. 1 presents a system, according to an embodiment.

As shown in FIG. 1, the server computer 100 may comprise at least one processor 102 and at least one memory 104 including a computer program code. According to an embodiment, the at least one memory 104 and the computer program code are configured, with the at least one processor 102, to cause the server computer 100 at least to provide and execute the web-based service 106 accessible by users via the network 120. The web service 106 comprises exercise data user accounts (UA), each exercise data user account comprising exercise data associated with a specific user. As such, there may be different user accounts for different users #1, #2, . . . , and #N. An example of such a web service 106 may be a Polar Personal Trainer (PTT), Polar Flow or iFIT service which comprises a database for storing the plurality of user accounts. It should be noted that the user accounts may be stored on a same or on different server computers.

The end users, or exercisers, may upload their training data from their exercise sensors or training computers to the corresponding user accounts. In an embodiment, the web service 106 may require that the users first connect to the web service 106 by applying a user name and a password, or other identification means. For this purpose, the web service 106 may comprise a login functional block 108 for establishing functionalities related to log in of the web service 106. Such functionalities may comprise checking of the user name and password combination against the stored information, for example. The user may then transfer, e.g., training data from their exercises devices 130 to 134 (e.g. exercise sensors or training computers) to the user accounts. The client may also change the settings of his/her exercise device(s) in the web service 106 and download the exercise device's settings from the web service 106 via the network 120 to the exercise device 130 to 134.

The training data, also known as physiological exercise data or exercise-related data, may have been stored during one exercise or during several exercises or physical activities and comprise training history including measurement data and accumulated performance data. The following is a non-limiting list of possible types of exercise data: heart rate zones, heart rate samples, heart rate variation samples, fat consumption, calorie consumption, activity zones, activity samples, speed and/or pace samples, power samples, cadence samples, altitude samples, temperature samples, location samples, pedal index, left-right balance, running index, training load, galvanic skin response samples, fluid balance, skin temperature samples. The user accounts may additionally store physiological data of the user and user attributes obtained from the user and/or the exercise device 130 to 134, such as name, gender, age, weight, height, fitness level, training schedule, maximum oxygen intake (VO2Max), maximum heart rate (HRMax), performance zones (heart rate zones, speed zones), aerobic and anaerobic thresholds. The user related data, such as the name or any of the other data items listed, may be used as a user identifier of the user of the exercise device (e.g. a sensor, a TC). As such, user records are transferred from the exercise device 130 to 134 to the web service 106 and to corresponding user accounts.

Figure 2:
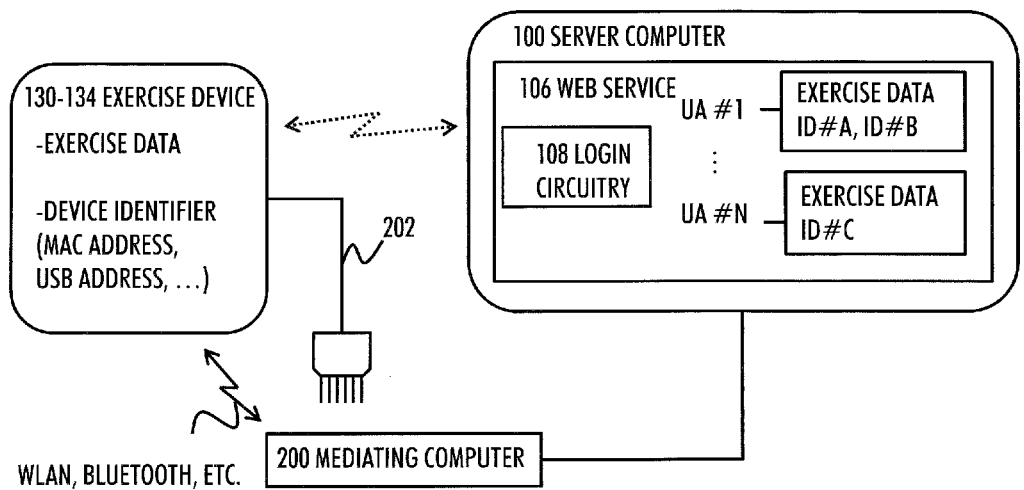
FIG. 2 shows how a connection between a physiological sensor device and a server computer may be provided, according to some embodiments.

As shown in FIG. 2, the transfer of the physiological exercise data from the exercise device(s) 130 to 134 may be performed wirelessly (e.g. WiFi, Bluetooth, Bluetooth low energy (BLE), infra-red, cellular network connection, etc.) or via a wire (e.g. universal serial bus 202) to a personal computer, or to any mediating device 200, which is used in accessing the back-end web service 106 behind the network 120. However, in one embodiment, the exercise device 130 to 134 may access the server computer 100 directly (e.g. wirelessly).

As such, the exercise data may be stored in the user's user account within the web service 106 so that the user may later analyze and view his/her exercise data, for example. However, in some cases it may be desirable that the user (i.e. the exerciser) may view or process the exercise data during the exercise from a user terminal 140 of FIG. 1, such as from a portable smart phone or a tablet. The benefits of doing so comprise viewing the exercise data in real time from a larger display than in a wrist held training computer, for example. The user terminal 140 may comprise, for example, an exercise data viewing application or any exercise application 150 designed for this purpose.

However, before enabling the viewing of the exercise data from the user terminal 140, the exercise data may need to be transferred to the user terminal 140, possibly wirelessly. For this, pairing of the exercise devices 130 to 134 with the user terminal 140 may need to be made. As said, often the pairing of devices is cumbersome due to user actions, for example. The user actions may comprise dialing of an access code, for example. Pairing, such as Bluetooth pairing, may also require that a certain technology is available in both of the devices. For example, in some cases, the user interface of at least one of the devices to be paired may be insufficient for pairing. Therefore, there is a need to optimize the pairing of devices.

Figure 3:
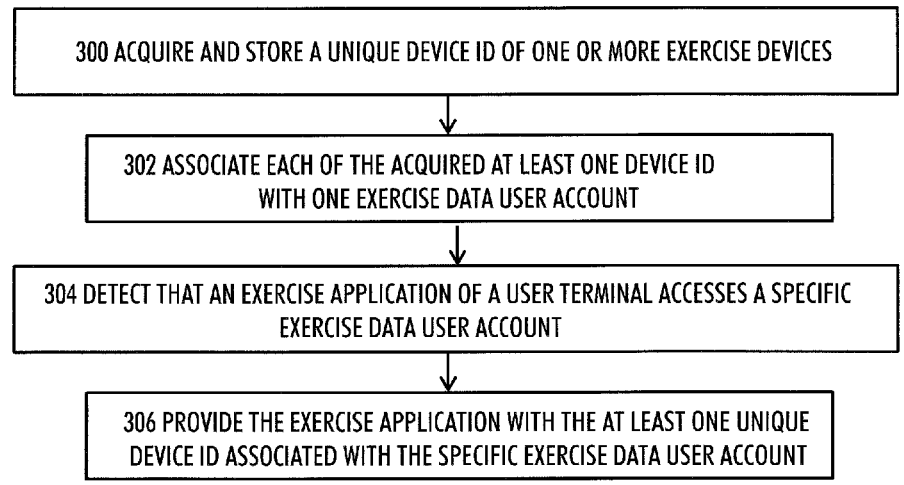
FIGS. 3 to 5 show methods, according to some embodiments.

Accordingly FIG. 1 shows a system for enabling user-friendly pairing of the user terminal 140 with at least one of the exercise devices 130 to 134. Let us first take a look at FIG. 3 in connection with FIG. 1. FIG. 3 shows actions performed by the server computer 100 in order to enable the proposed pairing process. In step 300 of FIG. 3 the server computer 100 may acquire and store a unique device identifier (ID) of at least one exercise device 130 to 134, wherein each exercise device 130 to 134 is portable and associated with a user having an exercise data user account. In FIG. 1, exercise devices 130 and 132 are associated with user #1, whereas the exercise device 134 is associated with user #2. It is assumed that at least the user #1 has a user account in the web service 106, as shown in FIG. 1.

The term portable "exercise device" may mean a training computer, a sports computer, any physiological sensor device, or any exercise sensor device. In an embodiment, the exercise device is a physiological sensor device. Example physiological sensor devices comprise sports/training computers having an integrated sensor (such as a GPS receiver or another motion sensor used for measuring speed and/or acceleration of the exercise), biosignal sensors (such as heart activity sensor and/or electromyogram (EMG) sensor), motion sensors (such as an accelerometer, a gyroscope, a stride sensor, a GPS receiver, a cadence sensor, and/or a magnetometer), biochemical sensors (such as a lactate sensor, a blood sugar sensor and/or hormone sensor), for example. It may be noted that, for example, a GPS receiver or another motion sensor used for measuring speed and/or acceleration of the exercise, such as of running or skiing, may be classified as one type of physiological sensor. It general, a physiological sensor device may comprise any sensor or any other equipment capable of monitoring, storing and/or recording at least some exercise data related to, associated with or applied during the exercise. Although some embodiments are written so that the user terminal 140 is paired with a physiological sensor device, the pairing could be between the user terminal 140 and any exercise device 130-134.

Figure 4:
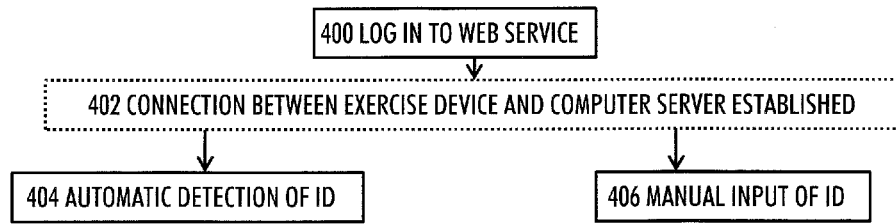

Let us look closer at how the IDs are acquired by the server computer 100 by referring to FIG. 4. For example, before the exercise, such as upon buying the physiological sensor device 130, the physiological sensor device 130 may be registered to the web service 106. This may take place such that the user accesses his/her user account stored in the server computer 100 by logging into the user account in step 400. Beforehand, the user may have installed required client software to the mediating device 200 and created his/her user account to the web service 106. The user login may follow the principles of a conventional web-based authentication, wherein the user inputs a user name and a password into appropriate fields provided in a web page related to the user accounts stored in the server computer 100. Other authentication means, such as biosignal or fingerprint authentication are also possible. This step may comprise operations in the mediating device 200 used for connecting the computer server 100, such as accessing a URL (Uniform Resource Locator) of the server computer 100 and communicating the user credentials to the server computer 100. This step may also comprise operations in the server computer 100, e.g. transmitting the web page to the mediating device 200, receiving the user credentials, and authenticating the credentials.

Thereafter, in step 402, the physiological sensor device 130 may be connected to the mediating device 200, such as a laptop, desktop, a tablet or mobile computer, and consequently a connection between the physiological sensor device 130 and the computer server 100 may be established, as described earlier in FIG. 2. In an embodiment, the step 402 may be performed before the step 400.

In an embodiment, the device identifier of the physiological sensor device 130 may then be transferred to the server computer 100 via the established connection between the physiological sensor device 130 and the server computer 100 via the mediating device 200. Accordingly, the acquisition of the unique device ID(s) from the physiological sensor device 130 may, as shown in step 404, be performed in an automatized procedure. In other words, the server computer 100, upon being connected to the exercise device 130 to 134, may automatically detect and fetch the uploaded device ID from the exercise sensor 130 or from the mediating device 200 (in case the device ID is already uploaded to the mediating device 200). As a consequence, no user input related to the transfer of the device ID is necessary.

In an embodiment, the user is required to be logged in to the user account before the detection of the ID is performed. In an embodiment, the web service 106 may request the user to confirm that the fetched at least one device ID is to be stored to the exercise data user account of the user in order to enhance security. In an embodiment, there may be an intermediate terminal or memory buffer which stores the detected device IDs and, upon confirmation and/or request of the user, uploads the device IDs to the corresponding user's exercise data user account.

In another embodiment, as shown in step 406, the user inputs the device ID manually into his/her user account in the web service 106. In this embodiment, the user may login to the web service 106 and to the corresponding user account without the exercise device 130 to 134 being connected to the server computer 100. Therefore, the step 402 may be omitted in this example embodiment.

In an embodiment, the unique device identifier is a device address or a portion thereof of the exercise device 130 to 134, e.g. a medium access control (MAC) address.

In another embodiment, the device identifier is an internet protocol address or a portion thereof of the exercise device 130 to 134. In yet another embodiment, the unique device identifier is a processor identification code or a portion thereof of the exercise device 130 to 134.

In an embodiment, the unique device ID is an electronic device identification number (DeviceID) laser printed on the training computer 132, for example. In yet one embodiment, the unique device identifier is a universal serial bus (USB) serial number or a portion thereof, wherein the USB is used to establish the connection from the exercise device 130 to 134. In an embodiment, the universal serial bus (USB) serial number, or a portion thereof, is the same as the electronic device identification number laser printed on the device. In an embodiment, the device ID is electronically readable through the USB from the serial number string of the USB Device Descriptor and also from the memory of the device. In an embodiment, the device ID is wirelessly readable from the memory of the device after paired connection with terminal device 140 and at least one of the exercise devices 130 to 134 has been accomplished In an embodiment, at least a portion of the unique device identifier indicates at least one of the following: sensor type, sensor manufacturer.

In step 302 of FIG. 3, the computer server 100 may associate each of the acquired at least one device ID with one of the exercise data user accounts of the web service 106, or with another addressed location specific to the user. Such association may be based on the user credentials of the user which has accessed certain user account. For example, the web service 106 of the server computer 100 may require the user to login before allowing an access to the exercise data user account. After such log in, the web service 106 may determine that the detected device ID is to be associated with the user account which has been accessed. In an embodiment, the computer server 100 may further detect the internet protocol (IP) address corresponding to the established connection and associate that IP address with that user account. Thereafter, the computer server 100 may associate each device ID acquired from that IP address with the corresponding user account.

The association of the device ID with the specific user account may be carried out by storing the device identifier into the user account or to another addressed location specific to the user, as shown in FIGS. 1 and 2. As a result, one user account may be associated with a plurality of device IDs (e.g. user account #1 is associated with IDs #A and #B), with one device ID (e.g. user account #N is associated with an ID #C), or with no device IDs.

In an embodiment, the computer server 100 may generate a list of device identifiers for each exercise data user account on the basis of the acquired at least one device identifier and the associations between the exercise data user accounts and the device ID(s). Thereafter, the computer server 100 may automatically update the lists each time a new device identifier is associated with the corresponding exercise data user account. This embodiment provides for an up-to-date ID lists.

In an embodiment, the lists may be periodically updated. The periodicity may be predetermined and based on empirical analysis, for example. In an embodiment, the computer server 100 may store the received IDs and the corresponding user account associations in a cache memory/buffer. Then the web service 106 may periodically update all the ID lists of all the user accounts of the web service 106 substantially simultaneously by uploading the stored IDs from the cache memory to the corresponding user accounts. Such procedure may simplify the process of updating the ID lists.

Thereafter, in step 304, the computer server 100 may detect that the exercise application 150 of the user terminal 140 of FIG. 1 accesses a specific exercise data user account in the web service 106. The user terminal 140 may be a smart phone, a tablet, a home computer, a cellular phone, for example. In an embodiment, the user terminal 140 is a portable user device. Again, the web service 106 may require that the user of the user terminal 140 provides user credentials, such as the user name and the password, before allowing the exercise application 150 to access the specific user account of the web service 106. Let us assume that the user terminal 140 belongs to user #1 and the exercise application 150 tries to access the user account (UA #1) of the user #1. In case correct user credentials are provided, the web service 106 may allow the access and assume that the user of the user terminal 140 is the user #1.

After such detection (step 304), the computer server 100 may, in step 306, provide the user terminal 140 with those at least one device identifier, which is associated with that specific exercise data user account. That is, the user terminal 140, after successfully accessing the specific user account (e.g. the UA #1), is provided with the device IDs which are associated with that user account (e.g. UA #1). In practice this may mean that all device IDs (or device-specific codes) associated with that user account (UA #1) in step 302 are copied from the user's account (UA #1) to the user terminal's 140 memory. This may be beneficial in order to allow the user terminal 140 to know which exercise devices 130 to 134 are allowed to wirelessly pair with the user terminal 140. Hence, a "white list" of access codes is formed in the memory of the user terminal 140. For example, the exercise device 134 belongs to user #2, as shown in FIG. 1. Therefore, the pairing to that device 134 should be avoided. Therefore, e.g., the device ID #C of the device 134 is not copied to the user terminal 140 of user #1. On the other hand, the devices 130 and 132 belong to the user #1. Therefore, the user terminal 140 may pair with those devices 130 to 132 and consequently the transferred "white list" comprises the device IDs #A and #B.

In one embodiment, the server computer 100 may acquire and store a user ID of the user of the exercise device 130 to 134. As said, e.g. the user name may represent the user ID. Alternatively, such user ID may be, e.g. the height/weight information, maximum oxygen intake, to mention only a few non-limiting examples. The computer server 106 may associate the user identifier with the exercise data user account corresponding to the user. Thus, the user records of one user are stored in his/her user account in the web service 106. Then, the computer server 100 may provide, in connection to step 306, the user terminal 140 with the user identifier which is associated with the accessed exercise data user account. This may be beneficial in case the user terminal 140 is a group user terminal, such as a tablet computer mounted on a gym device and used by different persons at different times. Then, the group user terminal 140 accessing the specific user account may acquire the user ID in addition to the "white list" of device IDs from the web service. The group user terminal 140 may then, e.g., display the acquired user ID on a display of the group user terminal 140. From the display, the current user of the group user terminal 140 may see that the group user terminal 140 is about to pair with the correct user or has paired with a correct person. In case wrong user ID is displayed, the current user may try the pairing process again.

Figure 5:
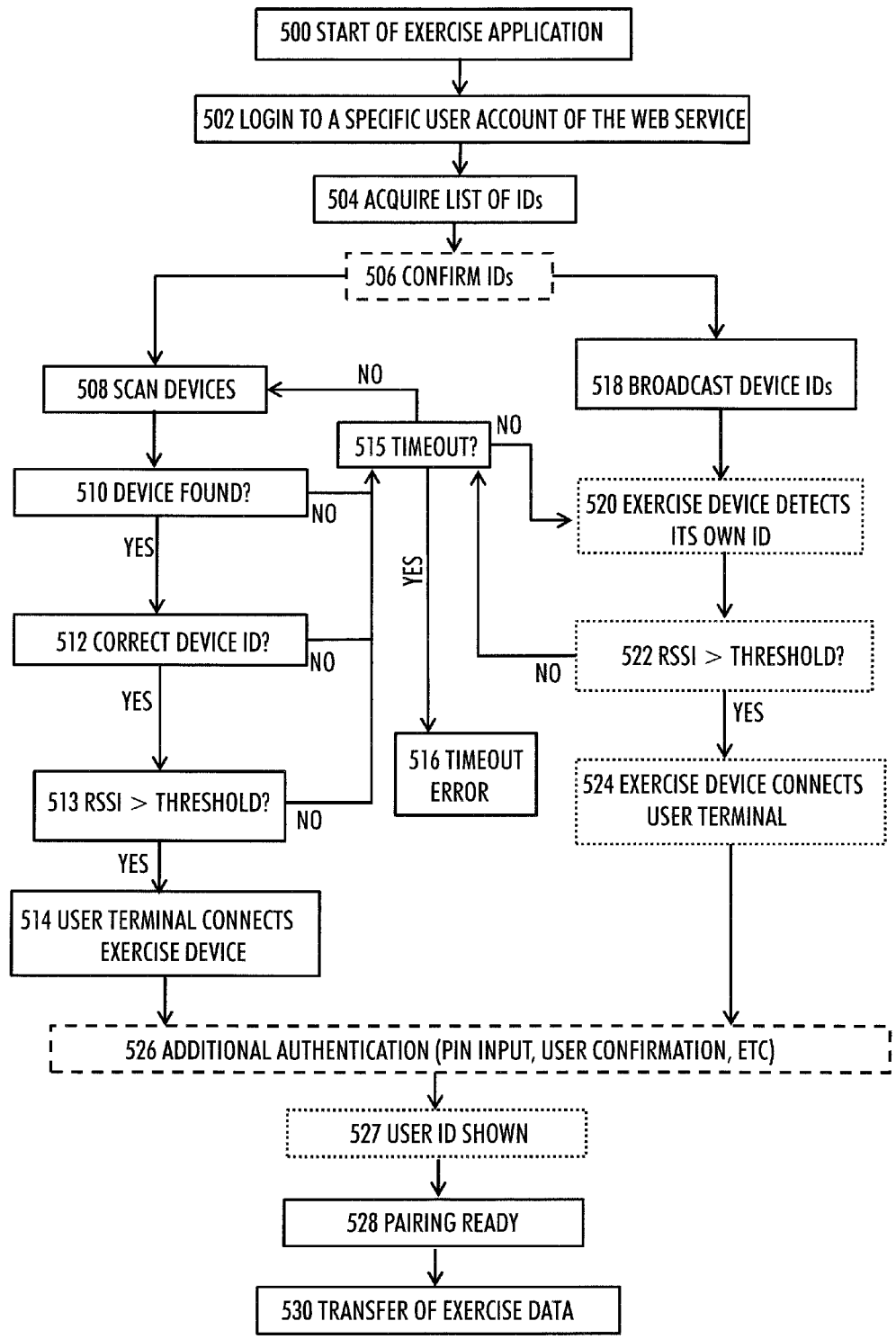

Let us now have a closer look on the operations of the user terminal 140 with reference to FIG. 5. In step 500, the user terminal 140 may execute the exercise application 150. The exercise application 150 may be a mobile exercise data viewing application, for example. In step 502, the user terminal 140, or more particularly, the exercise application 150, may successfully access the specific exercise data user account in the web service 106. Let us assume in this example that the user terminal 140 accesses the user account #1 because the user #1 is using the user terminal 140 and knows the login information of user account #1. In step 504, the user terminal 140 acquires the at least one device identifier from the web service 106, as explained earlier. Thereafter, the user terminal 140 may apply the acquired "white list" of device ID(s) in determining whether or not to allow the user terminal to wirelessly pair with the exercise device, as shown with reference numerals 508 to 528.

Optionally, in an embodiment, in step 506, the user terminal 140 may require the user to confirm that the at least one device ID (white list) acquired from the web service 106 is correct. For example, the user terminal 140 may indicate the acquired ID(s) on a display of the user terminal 140 and the user may check that the indicated ID(s) match with the ones printed on the exercise devices 130 to 132 of the user #1. Upon receiving the confirmation from the user, the user terminal 140 may accept the at least one device identifier as an identifier belonging to an exercise device 130, 132 with which pairing is allowed. As a consequence, the received "white list", including at least one device ID, is stored to the user terminal 140.

Let us look at how the utilization of the acquired device IDs in the wireless pairing process by the user terminal 140 may take place in different pairing topologies. As known by a skilled person, pairing may comprise establishment of a device-to-device communication connection between, e.g., the physiological sensor device 130 and the user terminal 140. Let us, as examples, consider a Bluetooth pairing topology. One embodiment, in which the exercise devices 130 to 134 take the peripheral role in pairing, is shown with reference numerals 508 to 516. Another embodiment, in which the user terminal 140 takes the peripheral role in the pairing, is shown with reference numerals 516 to 524.

Let us first consider the embodiment in which the exercise devices 130 to 134 take the peripheral role. In this embodiment, the user terminal 140 may, in step 508, start scanning of exercise devices in the proximity. The exercise devices 130 to 134 may all broadcast their device IDs so that receiving devices in the proximity (e.g. within a few meters) may detect the broadcasted device IDs. The exercise devices 130 to 134 may broadcast their own IDs continuously, periodically, or per user request, as the case may be. In an embodiment, the device ID is broadcasted as part of the peripheral role advertising data. The frequency used for the broadcasting may be predetermined in the standards, for example.

In step 510 the user terminal 140 may determine whether or not any exercise device is detected to be in the proximity. In case no devices are detected in the proximity, the process continues to step 515 in which it is detected whether or not a time period of a predefined length is expired. In case the time period has expired, a time out error occurs and such error may be displayed to the user in step 516 via the display of the user terminal 140. In case the time period is note expired, the user terminal 140 may continue scanning devices in step 508.

In case at least one exercise device is found in step 510, i.e. the user terminal 140 detects a device identifier broadcasted by at least one of the exercise devices 130 to 134, the process continues to step 512 in which it is determined whether or not the detected device ID is among the device identifier(s) acquired from the web service 106. In case the detected ID is not among the IDs on the "white list", the process continues to step 515, and consequently either to step 516 or to step 508, as explained before.

However, in case the detected device ID is one of the device IDs on the "white list", then the user terminal 140 may allow pairing with the exercise device. Let us assume that the physiological sensor device 130 is the one which has broadcasted the detected, allowed ID. Consequently, the process may continue to step 513.

In step 513, the user terminal 140 may determine received signal strength, such as the Bluetooth SIG specified Received Signal Strength Indicator (RSSI) or alike, from the physiological sensor device 130 with which pairing may be done. In an embodiment, the transmit power of the signal transmitted by any physiological sensor device 130 is the same. In an embodiment, the transmit power of the signal transmitted by any physiological sensor 130 may not be the same. However, in such case it may be that the transmitting device (e.g. the sensor 130 or training computer 132) includes an indication of the transmit power (Tx Power level) in the transmitted signal. In case the determined RSSI is lower than a predetermined threshold, derived empirically or on the basis of simulations, it may be determined that the distance to the physiological sensor device 130 is too long. Accordingly, the process may continue either to step 516 or to step 508, as explained before. However, if it is determined that the RSSI, or the signal strength in general, is above the predetermined threshold, the user terminal 140 may then continue to perform the pairing with the physiological sensor device 130. A high RSSI may denote that the physiological sensor device 130 is somewhat close to the user terminal 140. Such RSSI threshold may increase security of the pairing process. As a result, the user terminal 140 in the central role of the pairing process may connect the physiological sensor device 130 for pairing only when it receives an advertising packet including the correct device ID with sufficiently strong signal, which indicates that the distance between pairing devices is, e.g. 30 cm or less. The distance may be derived on the basis of the received signal strength, transmit power and known losses, for example. The connection may be initiated in step 514 by the device which is in the central role of the Bluetooth pairing, i.e. in the user terminal 140 in this embodiment.

In another embodiment, in which the user terminal 140 takes the peripheral role in the pairing, the user terminal 140 starts in step 518 broadcasting the at least one device ID, which it has received from the computer server 100. Depending on the number of IDs acquired, the user terminal 140 may broadcast one or many device IDs. The user terminal 140 may broadcast the device ID(s) so that the exercise devices listening in the proximity (e.g. within a few meters) may detect the broadcasted device IDs. The IDs may be broadcasted continuously, periodically, or per user request, as the case may be. In an embodiment, the device ID is broadcasted as part of the peripheral role advertising data.

Steps 520 to 524 depict actions of the exercise device (e.g. the physiological sensor device 130) acting in the central role of the pairing process. In step 520, the physiological sensor device 130 detects the device ID #A being broadcasted by the user terminal 140. It may be noted that device ID #A is the one corresponding to the physiological sensor device 130. Thus, after detecting its own device ID #A, the physiological sensor device 130 may check in step 522 whether or not the received signal strength of the signal carrying the device ID from the user terminal 140 is above a predetermined signal strength threshold, such as above the Bluetooth SIG specified Received Signal Strength Indicator (RSSI) or alike. In case the RSSI is lower than a predetermined threshold, then it may be determined that the distance to the user terminal 140 is too long. Accordingly, the process may continue either to step 516 or back to step 520, depending is the time period reserved for the pairing process expired or not in step 515, as explained earlier. However, if it is detected that the RSSI, or the signal strength in general, is above the predetermined threshold, the physiological sensor device 130 may then continue to perform the pairing with the user terminal 140 by connecting the user terminal in step 524. The user terminal 140 may thus receive a request for the connection establishment from the physiological sensor device 130.

Optionally, in an embodiment, there may be additional authentication requirements in step 526. These may include the exercise application 150 is required to confirm that the device ID of the connecting physiological sensor device 130 is the among the "white list" by reading the device ID from the mass memory of the physiological sensor device 130 when the physiological sensor device 130 connects the user terminal 140 in step 524. In an embodiment, such reading may take place with a generic attribute (GATT)-based proprietary file transfer protocol of the Bluetooth protocol in order to ensure secure reading. Further additional authentication may comprise input of PIN codes or user confirmations. However in an embodiment, no user input is required for the pairing process. In an embodiment, the physiological sensor device 130 does not have a user interface. Accordingly, automatic pairing may be beneficial.

In an embodiment, optionally, in step 527, the user terminal may show the user ID, such as the name of the user or some other user data from which the user may identify him/herself, on the display of the user terminal 140.

In an embodiment, the user may be asked to start the broadcast of the device ID either in the user terminal 140 or in the physiological sensor device 130. The request may be outputted to the user via the display of the user terminal 140, for example. The user may be also asked to bring the devices 130 and 140, between which the pairing is to be performed, close to each other.

As a result, in step 528, the wireless pairing between the user terminal 140 and the physiological sensor device 130 is ready and a device-to-device connection is established. Similarly, pairing may be performed between the exercise device 132 and the user terminal 140. This is because both of these are devices of the user #1 and, consequently, the list of device IDs obtained by the user terminal 140 comprises the device ID #B of the exercise device 132. However, as shown in FIG. 1, connection establishment between the user terminal 140 and the exercise device 134 may not take place because the device ID #C of the exercise device 134 is not among the "white list" of IDs for the user #1.

In an embodiment, in case of finding several physiological sensors with device IDs on the white list, the one which is detected to be closer, on the basis of the transmit power and received signal strength, may be paired first, for example.

After the pairing the exercise application 150 of the user terminal 140 may perform further control of the rest of the communication between the user terminal 140 and the paired devices. In an embodiment, the pairing data is saved and used for future connections to find correct peripheral role advertising device(s). The saved data may comprise identity resolving keys, BDA (public Bluetooth Address) or other device identifiers supported by the Bluetooth protocol, for example. The saved data may later be used in allowing pairing with a detected device having a known device ID even if the received signal strength of that detected device is below the received signal threshold, for example. Although explained that the pairing applies the Bluetooth protocol, the pairing may apply some other communication technology, such as WiFi through wireless local area network.

In an embodiment, after the pairing is done in step 528, the exercise application 150 and the exercise device 130, 132 are configured to handle and transfer exercise data of the user in step 530.

In an embodiment, the training computer 132 may comprise a memory for each device (e.g. each sensor) it has been paired with. At least an indication (such as the device ID) of the paired devices may also be transferred to the web service 106, and more particularly to the user account corresponding to the user of the training computer 132. As the user terminal 140 of the same user accesses the same user account, the web service 106 may upload this information to the user terminal 140. In this manner the user terminal 140 acquires knowledge of the devices that have been paired with the training computer. An example use for using this acquired information may be that the user terminal 140 may detect a data transfer between the training computer 132 and at least one of the devices that have been paired with the training computer 132. It may be noted that during such data transfer, the training computer 132 may not be paired with the user terminal 140. However, the user interface of the user terminal 140 may advantageously indicate to the user that the data transfer may be temperately stopped so that the pairing between the user terminal 140 and the training computer 132 may be performed. This may be especially useful when the training computer 132 does not have a display of its own.

FIG. 1 further shows that the user terminal 140 comprises a control circuitry (CTRL) 142, such as at least one processor, and at least one memory 144 including a computer program code (PROG), wherein the at least one memory 144 and the computer program code (PROG), are configured, with the at least one processor 142, to cause the user terminal 140 to carry out any one of the described processes.

The memory 144 (and the memory 104) may be implemented using any suitable data storage technology, such as semiconductor based memory devices, flash memory, magnetic memory devices and systems, optical memory devices and systems, fixed memory and removable memory.

The control circuitry 142 may comprise a pairing circuitry 152 for performing any of the functionalities related to the pairing process, according to any of the embodiments. The control circuitry 142 may further execute the exercise application 150.

The user terminal 140 may further comprise communication interface (TRX) 148 comprising hardware and/or software for realizing communication connectivity according to one or more communication protocols. The TRX 148 may provide the user terminal 140 with communication capabilities to access the radio frequency network, for example. The user terminal 140 may also comprise a user interface 146 comprising, for example, at least one of a keypad, a microphone, a touch display, a display, a speaker, etc. Similar user interface and communication interface may be comprised in the server computer 100 as well. Also the exercise devices 130 to 134 may comprise similar communication interface.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

The invention claimed is:

1. A system, comprising:
a server computer comprising at least one processor and at least one memory including a computer program code, wherein the at least one memory and the computer program code are configured, with the at least one processor, to cause the server computer to perform operations comprising:
providing a web service accessible by users via a network, wherein the web service comprises a plurality of exercise data user accounts and a database for storing the plurality of exercise data user accounts, and wherein each exercise data user account is for storing physiological exercise data associated with a specific user;
acquiring and storing a unique device identifier of at least one physiological sensor device, wherein each physiological sensor device is portable and associated with a user having an exercise data user account;
associating each of the acquired at least one device identifier with one of the plurality of exercise data user accounts;
detecting that an exercise application of a user terminal successfully accesses a specific exercise data user account of the plurality of exercise data user accounts;
providing the user terminal with the at least one device identifier previously associated with the specific exercise data user account of the plurality of exercise data user accounts in response to detecting that the exercise application of the user terminal successfully accesses the specific exercise data user account of the plurality of exercise data user accounts to enable the user terminal to determine which physiological sensor device is allowed to wirelessly pair with the user terminal;
acquiring physiological exercise data of a user from the at least one physiological sensor device;
storing said physiological exercise data to the exercise data user account associated with said at least one physiological sensor device, the physiological exercise data comprising at least one of the following data: heart rate zone data, speed zone data, activity zone data, cadence sample data, pedal index data, left-right balance data, running index data, training load data, and fluid balance data; and
detecting the device identifier, which has already been uploaded to a mediating device prior to the server computer being connected to the physiological sensor device, automatically while the physiological sensor device is connected to the mediating device, which is used in accessing the web service.

2. The system of claim 1, wherein the server computer is further caused to perform operations comprising:

acquiring the device identifier during the user being logged in to the exercise data user account of the user;

requiring a user login before allowing an access to the exercise data user account; and determining the exercise data user account, to which the device identifier is to be associated with, on the basis of login information of the web service.

3. The system of claim 1, wherein the server computer is further caused to perform operations comprising:

generating a list of device identifiers for each exercise data user account on the basis of the acquired at least one device identifier and the associations between the exercise data user accounts and the device identifiers; and automatically updating the lists each time a new device identifier is associated with the corresponding exercise data user account.

4. The system of claim 1, wherein the server computer is further caused to perform operations comprising:

acquiring and storing a user identifier of the user of the physiological sensor device;

associating the user identifier with the exercise data user account corresponding to the user; and providing the user terminal with the user identifier which is associated with the accessed exercise data user account.

5. The system of claim 1, wherein the exercise application, the web service and the physiological sensor device are configured to handle and transfer physiological exercise data of the user.

6. The system of claim 1, wherein the system further comprises:

the user terminal comprising at least one processor and at least one memory including a computer program code, wherein the at least one memory and the computer program code are configured, with the at least one processor, to cause the user terminal to perform operations comprising:

successfully accessing a specific exercise data user account in the web service;

acquiring the at least one device identifier from the web service; and applying the acquired at least one device identifier in determining whether or not to allow the user terminal to wirelessly pair with a physiological sensor device.

7. The system of claim 6, wherein the user terminal is further caused to perform operations comprising:

requiring the user of the user terminal to confirm that the at least one device identifier acquired from the web service is correct; and upon receiving the confirmation from the user, accepting the at least one device identifier as an identifier belonging to a physiological sensor device with which pairing is allowed.

8. The system of claim 6, wherein the user terminal is further caused to perform operations comprising:

detecting a device identifier broadcasted by the physiological sensor device;

determining whether or not the detected device identifier of the physiological sensor device is among the at least one device identifier acquired from the web service; and performing pairing of the user terminal with the physiological sensor device upon determining that the detected device identifier of the physiological sensor device is among the at least one device identifier acquired from the web service.

9. The system of claim 6, wherein the user terminal is further caused to perform operations comprising:

broadcasting the at least one device identifier acquired from the web service;

receiving a request for a connection establishment from a physiological sensor device which has detected that the broadcasted device identifier corresponds to the device identifier of that physiological sensor device; and performing pairing of the user terminal with that physiological sensor device.

10. The system of claim 6, wherein the user terminal is further caused to perform operations comprising:

determining received signal strength from the physiological sensor device; and performing the pairing with the physiological sensor device only if the received signal strength from the physiological sensor device is above a predetermined threshold.

11. The system of claim 6, wherein the user terminal is further caused to perform operations comprising:

acquiring the user identifier from the web service; and displaying the user identifier on a display of the user terminal.

12. The system of claim 6, wherein the user terminal is one of the following: a personal computer, a portable phone, a portable tablet computer.

13. The system of claim 1, wherein the unique device identifier comprises at least a portion of a medium access control, MAC, address or a universal serial bus, USB, serial number.

14. The system of claim 1, wherein at least a portion of the unique device identifier indicates at least one of the following: sensor type, sensor manufacturer.

15. The system of claim 1, wherein the physiological sensor device does not have a user interface integrated therein.

16. A user terminal, comprising:

at least one processor and at least one memory including a computer program code, wherein the at least one memory and the computer program code are configured, with the at least one processor, to cause the user terminal to perform operations comprising:

successfully accessing a specific exercise data user account in a web service via a network, wherein the web service comprises a plurality of exercise data user accounts and a database for storing the plurality of exercise data user accounts, and wherein each exercise data user account is for storing physiological exercise data associated with a specific user;

acquiring at least one unique device identifier from the web service in response to successfully accessing the specific exercise data user account of the plurality of exercise data user accounts, wherein the acquired at least one device identifier is previously associated with the specific exercise data user account and corresponds to at least one portable physiological sensor device;

applying the acquired at least one device identifier in determining whether or not to allow the user terminal to wirelessly pair with a physiological sensor device, physiological exercise data of a user being acquired from the at least one physiological sensor device, said physiological exercise data being stored to the exercise data user account associated with said at least one physiological sensor device, the physiological exercise data comprising at least one of the following data: heart rate zone data, speed zone data, activity zone data, cadence sample data, pedal index data, left-right balance data, running index data, training load data, and fluid balance data; and detecting the device identifier, which has already been uploaded to a mediating device prior to the server computer being connected to the physiological sensor device, automatically while the physiological sensor device is connected to the mediating device, which is used in accessing the web service.

17. The user terminal of claim 16, wherein the user terminal is further caused to perform operations comprising:
requiring the user of the user terminal to confirm that the at least one device identifier acquired from the web service is correct; and
upon receiving the confirmation from the user, accepting the at least one device identifier as an identifier belonging to a physiological sensor device with which pairing is allowed.

18. The user terminal of claim 16, wherein the user terminal is further caused to perform operations comprising:
detecting a device identifier broadcasted by the physiological sensor device;
determining whether or not the detected device identifier of the physiological sensor device is among the at least one device identifier acquired from the web service; and
performing pairing of the user terminal with the physiological sensor device upon determining that the detected device identifier of the physiological sensor device is among the at least one device identifier acquired from the web service.

19. The user terminal of claim 16, wherein the user terminal is further caused to perform operations comprising:
broadcasting the at least one device identifier acquired from the web service;
receiving a request for a connection establishment from a physiological sensor device which has detected that the broadcasted device identifier corresponds to the device identifier of that physiological sensor device; and
performing pairing of the user terminal with that physiological sensor device.

20. The user terminal of claim 16, wherein the user terminal is further caused to perform operations comprising:
acquiring a user identifier from the web service, wherein the user identifier corresponds to the user of the physiological sensor and is associated with the specific exercise data user account; and
displaying the user identifier on a display of the user terminal.

21. The user terminal of claim 16, wherein the user terminal is one of the following: a personal computer, a portable phone, a portable tablet computer.

22. A computer program product embodied on a non-transitory distribution medium readable by a computer and comprising program instructions which, when executed by an apparatus, cause the apparatus at least to perform operations comprising:
successfully accessing a specific exercise data user account in a web service via a network, wherein the web service comprises a plurality of exercise data user accounts and a database for storing the plurality of exercise data user accounts, and wherein each exercise data user account is for storing physiological exercise data associated with a specific user;
acquiring at least one unique device identifier from the web service in response to successfully accessing the specific exercise data user account of the plurality of exercise data user accounts, wherein the acquired at least one device identifier is previously associated with the specific exercise data user account and corresponds to at least one portable physiological sensor device;
applying the acquired at least one device identifier in determining whether or not to allow the apparatus to wirelessly pair with a physiological sensor device, the physiological exercise data of a user being acquired from the at least one physiological sensor device, said physiological exercise data being stored to the exercise data user account associated with said at least one physiological sensor device, the physiological exercise data comprising at least one of the following data: heart rate zone data, speed zone data, activity zone data, cadence sample data, pedal index data, left-right balance data, running index data, training load data, and fluid balance data; and
detecting the device identifier, which has already been uploaded to a mediating device prior to the server computer being connected to the physiological sensor device, automatically while the physiological sensor device is connected to the mediating device, which is used in accessing the web service.

23. The system of claim 1, wherein the server computer is further caused to perform operations comprising:
detecting an IP address associated with a connection and associating the detected IP address with the exercise data user account.

* * * * *

UNITED STATES PATENT AND TRADEMARK OFFICE
CERTIFICATE OF CORRECTION

PATENT NO. : 9,705,989 B2
APPLICATION NO. : 14/026519
DATED : July 11, 2017
INVENTOR(S) : Sipola et al.

It is certified that error appears in the above-identified patent and that said Letters Patent is hereby corrected as shown below:

In the Specification

Column 3, Line 66: now reads "It general, a physiological" should read -- In general, a physiological --

Column 8, Line 1: now reads "is note expired" should read -- is not expired --

Column 9, Line 15: now reads "depending is the time" should read -- depending if the time --

Signed and Sealed this
Twentieth Day of February, 2018

Andrei Iancu
*Director of the United States Patent and Trademark Office*